United States Patent [19]

Buysch et al.

[11] 4,012,406

[45] Mar. 15, 1977

[54] PROCESS FOR THE PREPARATION OF DIARYL CARBONATES

[75] Inventors: Hans Josef Buysch, Krefeld-Bockum; Heinrich Krimm, Krefeld, both of Germany

[73] Assignee: Bayer Aktiengesellschaft, Germany

[22] Filed: Sept. 30, 1975

[21] Appl. No.: 618,057

[30] Foreign Application Priority Data

Oct. 10, 1974 Germany .................... 2447348

[52] U.S. Cl. .................... 260/463; 260/295 R; 260/295.5 R

[51] Int. Cl.² .................... C07C 68/02

[58] Field of Search ......... 260/463, 295 R, 295.5 R

[56] References Cited

UNITED STATES PATENTS

| 2,837,555 | 6/1958 | Lee | 260/463 |
|---|---|---|---|
| 3,170,946 | 2/1965 | Kilsheimer | 260/463 |
| 3,211,774 | 10/1965 | Stephens | 260/463 |
| 3,211,775 | 10/1965 | Stephens et al. | 260/463 |
| 3,211,776 | 10/1965 | Stephens | 260/463 |

*Primary Examiner*—Lewis Gotts
*Assistant Examiner*—D. R. Phillips
*Attorney, Agent, or Firm*—Connolly and Hutz

[57] ABSTRACT

A process for the preparation of a diaryl carbonate by the reaction of an aromatic monohydroxy compound with phosgene under elimination of hydrogen chloride, wherein said reaction is carried out in the presence of a catalytic quantity of an aromatic heterocyclic basic nitrogen compound, or a salt thereof, or an adduct thereof formed under the reaction conditions.

9 Claims, No Drawings

PROCESS FOR THE PREPARATION OF DIARYL CARBONATES

This invention relates to a process for the preparation of diaryl carbonates by the reaction of an aromatic monohydroxy compound with phosgene with the elimination of hydrogen chloride in the presence of a catalytic quantity of an aromatic, heterocyclic basic nitrogen compound.

It is known that diaryl carbonates can be obtained from aromatic hydroxy compounds by phase boundary phosgenation Schotten-Baumann reaction). In this reaction, the use of solvents and caustic soda has a harmful effect because soda is liable to cause partial saponification of phosgene. In addition, the large quantities of sodium chloride produced in the reaction cause a pollution problem in the effluent water.

It has therefore been proposed to carry out a solvent-free condensation in the presence of tetramethyl ammonium halides as catalysts according to the U.S. Pat. No. 2,837,555. This process, however, requires relatively large quantities of catalyst, generally 5 to 7% by weight, based on the quantity of phenol to achieve economic reaction velocities and it is also necessary to employ relatively high reaction temperatures of between 180° C and 215° C, which entails the risk of decomposition of the thermally unstable tetramethyl ammonium halides. Moreover, the catalyst must subsequently be removed by washing with water, which makes recovery very much more difficult. Another disadvantage is that much more than the stoichiometric quantity of phosgene is used up. The yields of diphenyl carbonate are little more than 80% of the theory.

In another known process, described in U.S. Pat. No. 3,234,263, diphenyl carbonates are obtained by heating phenyl chlorocarbonic acid esters in the presence of large quantities of alkali metal or alkaline earth metal compounds and basic tertiary nitrogen compounds as catalysts. This process has the disadvantage of requiring high temperatures to be employed if even moderately economic reaction times are to be achieved. At these high temperatures, half the original quantity of phosgene put into the process is lost in the form of carbon dioxide. Moreover, the chlorocarbonic acid ester must be synthesised in a separate process step. Since, moreover, it is well known that phenyl chlorocarbonic acid esters change into diphenyl carbonates at temperatures of only 180° C with the elimination of phosgene, the catalytic action of the additives would appear to be doubtful (Compt. rend. 128, 1579).

It has now been found that aromatic heterocyclic basic nitrogen compounds are much more effective catalysts for the reaction of aromatic monohydroxy compounds with phosgene to produce diaryl carbonates than the known tetramethyl ammonium halides.

This invention therefore relates to a process for the preparation of diaryl carbonates by the reaction of aromatic monohydroxy compounds with phosgene under the elimination of hydrogen chloride wherein said reaction is carried out in the presence of catalytic quantities of at least one aromatic heterocyclic basic nitrogen compound or its salts or adduct formed under the reaction conditions, preferably at a temperature range of 25° to 200° C.

The use of aromatic basic nitrogen compounds such as pyridine or quinoline for the preparation of diaryl carbonates is already known, but, according to the known processes at least equimolar quantities of these basic compounds have been used to bind the hydrogen chloride eliminated because it was thought that the resulting salt is catalytically inactive (see also H. Schnell: Polymer Reviews, volume 9, pages 11 and 12 John Wiley and Sons, 1964).

In view of this prior art, it is surprising that the chlorides of heterocyclic bases which are formed immediately after addition of the free bases to the reaction mixture are active in catalytic quantities even at 25° C. Although at this temperatures no thermal dissociation of the hydrochlorides occurs, they are highly efficient in catalysing the formation of diaryl carbonate. Under otherwise comparable conditions, the reaction proceeds much more rapidly than in the process according to U.S. Pat. No. 2,837,555. The reaction velocity is more than twice as high, even at much lower temperatures.

Another advantage of the inventive process is that the catalyst can be separated from the reaction mixture. This can be carried out by various methods.

The reaction mixture may either be distilled under vacuum, in which case the catalyst is left behind as sump product in the form of a readily fusible adduct, or the adduct obtained in this way is removed in crystalline form by filtration at moderate temperatures (about 50° to 100° C) or as melt at higher temperatures. In any event the isolated compounds can immediately be used again as catalysts. It is generally sufficient to use 1 mol of phosgene for 2 mols of phenol if the phosgene is not driven off with the hydrogen chloride evolved. If it is driven off in this way, it may either be recovered by the usual methods or the exhaust gas may be passed through a fresh mixture of phenol and catalyst, in which the excess phosgene is bound quantitatively Suitable starting materials for the process according to the invention are aromatic monohydroxy benzenes containing 6 to 16 carbon atoms such as phenol, o-, m- and p-cresol, o-, m-, and p-isopropyl phenol, the corresponding halogenated phenols and alkoxy phenols such as p-chlorophenol and p-methoxyphenol, monohydroxy compounds containing condensed benzene rings such as of naphthalene, anthracene and phenanthrene and monohydroxy compounds of heterocyclic ring compounds with 5 to 6 ring members which may also be condensed or substituted with carbocyclic radical, for example 4-hydroxypyridine.

The catalysts used may be any basic nitrogen compounds in which the nitrogen atom is contained in an aromatic 5- or 6-membered ring and which do not have any other functional groups (e.g. $NH_2$ or OH-groups) which are liable to form firm bonds with phosgene or carbonates under the reaction conditions. In addition to the nitrogen atom, the ring may contain other hetero atoms such as oxygen, sulphur or a second nitrogen atom. The heterocyclic radical may also be condensed with other aromatic heterocyclic radicals or with aromatic carbocyclic radicals.

The following are mentioned as examples of such catalysts which may be used according to the invention: pyridine; quinoline; isoquinoline; picoline; acridine; pyrazine; pyridazine; pyrimidine and the corresponding benzoheterocyclic compounds in which the benzene ring may be substituted with inert groups such as alkyl, carbalkoxy, halogen or the like; oxazines; thiazines such as phenothiazine; triazines such as 2,4,6-trimethyltriazine; compounds of this kind which are substituted with alkyl; alkoxy; carbalkoxy or halogen, such as 2-methyl-imidazole, and the corresponding benzoheterocyclic compounds such as benzimidazole; benzotriazole and benzothiazole. The preferred catalysts are pyridine; quinoline; picoline; imidazoles; benzimidazoles; pyrazoles; triazoles and benzotriazoles. They are used preferably in quantities of 0.1 to 10% by weight, based on the reaction mixture, more preferably 1 to 3% by weight.

The catalysts according to the invention are, of course, instantly converted into the corresponding hydrochlorides in the reaction mixture. On the other hand, many of the basic nitrogen compounds mentioned are in a state of dissociation equilibrium between the salt form and the free base, the balance depending on the strength of the base and the temperature. Salts of the bases may therefore be used instead of the free bases without jeopardising the effects according to the invention, for example, their hydrochlorides, hydrobromides, sulphates or nitrates or salts from which the hydrochlorides are easily formed in the reaction mixture, for example, formates; acetates; phosphates; carbamates or picrates.

The process according to the invention is preferably carried out by introducing phosgene under normal pressure, or at elevated or reduced pressure if desired, into the mixture of melt and catalyst by means of the usual gas distributing apparatus such as frits, perforated plates (for example in bubble column reactors) or gasification stirrers. An intimate mixture of gas and melt can also be obtained by passing them in counter-current to each other in columns of filling bodies.

Solvents may be used if desired. They should be inert under the reaction conditions and dissolve the starting compounds. Suitable solvents include, for example, aromatic, optionally halogenated, hydrocarbons containing 6 to 16 carbon atoms, such as xylene; cumene and diisopropyl benzene, chlorobenzene and dichlorobenzene and aliphatic halogenated hydrocarbons such as trichloroethylene; methylene chloride and tetrachloroethylene. They are preferably used in cases where the desired diaryl carbonates are to be purified by recrystallisation. Reaction in that case takes place in a suitable solvent.

The process according to the invention is carried out preferably at a temperature of from 25° to 200° C, more preferably at 40° to 180° C. It may be carried out either discontinuously or continuously.

Isolation and purification of the diaryl carbonates are carried out by known methods, e.g. distillation or recrystallisation.

The diaryl carbonates prepared according to the invention are suitable for the preparation of polycarbonates by the solvent-free trans-esterification process, for the preparation of phenyl urethanes, as herbicides or for the removal of water from sensitive substances.

EXAMPLE 1 a. A mixture of 282 g (3 mol) of phenol and 6.6 g (3.2 mol-% per mol of phenol) of imidazole is gasified with a uniform stream of phosgene through a frit for 1½ hours. The temperature, which is initially 150° C, rises continuously to 175° C during this time. The total quantity of phosgene introduced is 145 g. At the end of this time, 98.2% of the phenol has been converted into diphenyl carbonate. No by products are found.

The catalyst settles to the bottom of the yellowish melt as a second yellow phase in the form of an adduct which can be separated and immediately used again in a fresh batch. The quantitative conversion of the above quantity of phenol to diphenyl carbonate requires 1.5 mol of phosgene (135 g). Only 10 g more than the calculated quantity of phosgene are used up for practically complete conversion of phenol. This means that phosgene reacts with extreme rapidity in the presence of this catalyst since hardly any of it is carried away with the hydrogen chloride in spite of the vigorous evolution of hydrogen chloride. The total quantity of phosgene used is thus 48.4 g per mol of phenol.

In Examples 1 and 2 of U.S. Pat. No. 2,837,555, on the other hand, 99.5 g of phosgene are introduced per mol of phenol, that is to say 1 mol of phosgene per mol of phenol to obtain a similar high degree of conversion. It must be concluded from this that either excess phosgene escapes unused with the hydrogen chloride; the excess phosgene is first used up in the formation of phenyl chloroformic acid ester and subsequently split off again or that it is used up in side reactions.

b. The diphenyl carbonate obtained according to (a) is purified by distillation and used for the preparation of a polycarbonate as follows:

A mixture of 45.6 parts by weight of 2,2-bis-[4hydroxyphenyl]-propane, 47.1 parts by weight of diphenyl carbonate and 0.008 parts by weight of lithium hydride is slowly heated to 210° C at 20 Torr, the major portion of phenol split off in the reaction being distilled off. The pressure is then reduced to 0.2 Torr and the temperature is raised to 250° C over a period of 1 hour and to 280° C over a period of two further hours. Towards the end of condensation, the catalyst is neutralised by stirring 0.05 parts by weight of dimethyl sulphate into it. The excess dimethyl sulphate is removed under vacuum by further heating. The highly viscous melt solidifies on cooling to a colourless, elastic resin which softens at about 240° C. The average molecular weight determined viscosimetrically is in the region of 30 000.

Comparison experiment for example 1

A mixture of 282 g (3 mol) of phenol and 11.5 g (3.2 mol % per mol of phenol) of tetramethyl ammonium chloride (corresponding to the proportions given in example 2 of U.S. Pat. No. 2.837,555) is gasified with 145 g of phosgene over a period of 1½ hours as in example 1, the temperature rising during this time from 150° C to 175° C. At the end of this time, the reaction mixture contains only 21% of diphenyl carbonate.

The two examples show that for a given molar concentration of catalyst, the temperature required is lower and the reaction time shorter than in the examples given in U.S. Pat. No. 2,837,555, where 3.2 mol percent of catalyst are used per mol of phenol. The comparison experiment demonstrates the substantially lower activity of tetramethyl ammonium compounds compared with that of catalysts according to the invention under completely comparable conditions.

EXAMPLE 2

The experiment is carried out in a manner analogous to example 1 (a) except that 12.5 g (3.2 mol-% per mol of phenol) of quinoline are used as catalyst instead of imidazole. The reaction temperature is raised from 155° C to 167° C over a period of 1¾ hours and a total of 170 g of phosgene is introduced. The resulting reaction mixture consists of 92.8% of diphenyl carbonate and 7.2 g of phenyl chlorocarbonic acid ester, apart from catalyst.

EXAMPLE 3

A mixture of 188 g (2 mol) of phenol, 3.5 g of imidazole and sufficient toluene to produce a liquid phase at 25° C is gasified with a very weak stream of phosgene at 20° to 25° C for 8 hours. The resulting reaction mixture contains 12% of diphenyl carbonate.

EXAMPLE 4

A mixture of 282 g (3 mol) of phenol and 5.5 g of imidazole is gasified with a weak stream of phosgene at 100° C for 8 hours. 71% of the phenol put into the reaction are converted into diphenyl carbonate. After distillation of the reaction product at 3 to 4 Torr, 14 g of yellow residue is left which shows the same catalytic properties as imidazole when the experiment is repeated.

EXAMPLE 5

The procedure is the same as in example 4, except that 15 g of pyridine are used as catalyst instead of imidazole. The reaction mixture contains 40 % of diphenyl carbonate after 3½ hours.

EXAMPLE 6

Example 4 is repeated but with 7 g of imidazole as catalyst. The reaction is stopped after 3 hours (24% of diphenyl carbonate) and the mixture is left to cool. 17 g of yellowish crystals (melting point 187° to 189° C) are obtained by suction filtration and washing with toluene. When used in the next batch, they show the same catalytic activity as imidazole.

We claim:

1. A process for the preparation of a diaryl carbonate by the reaction of an aromatic monohydroxy compound with phosgene under elimination of hydrogen chloride, wherein said reaction is carried out in the presence of a catalytic quantity of an aromatic heterocyclic basic nitrogen compound selected from the group consisting of pyridine, quinoxaline, imidazole, benzimidazole, pyrazole, triazole and benztriazole, or a salt thereof, or an adduct thereof formed under the reaction conditions.

2. A process as claimed in claim 1, wherein the reaction is carried out at a temperature of from 25° to 200° C.

3. A process as claimed in claim 1, wherein 2 mols of aromatic monohydroxy compound are used per mol of phosgene.

4. A process as claimed in claim 1, wherein the aromatic monohydroxy compound contains from 6 to 16 carbon atoms.

5. A process as claimed in claim 4, wherein the aromatic monohydroxy compound is phenol, 0-, m- or p-cresol, o-, m- or p-isopropyl phenol, which phenols may be substituted by halogen or alkoxy; a monohydroxy compound of naphthalene, anthracene, phenanthrene or a heterocyclic radical with 5 to 6 ring members which may be condensed or substituted with a carbocyclic radical.

6. A process as claimed in claim 1, wherein the aromatic heterocyclic basic nitrogen compound is used is a quantity of from 0.1 to 10% by weight, based on the reaction mixture.

7. A process as claimed in claim 6, wherein the aromatic heterocyclic basic nitrogen compound is used in a quantity of from 1 to 3% by weight, based on the reaction mixture.

8. A process as claimed in claim 1, wherein the reaction is carried out in the presence of a solvent.

9. A process as claimed in claim 8, wherein the solvent is an aromatic hydrocarbon containing 6 to 16 carbon atoms, which may be halogenated or an aliphatic halogenated hydrocarbon.

* * * * *